(12) United States Patent
Riethmüller

(10) Patent No.: US 8,798,935 B2
(45) Date of Patent: Aug. 5, 2014

(54) IMAGING METHOD AND USE THEREOF

(76) Inventor: Christoph Riethmüller, Münster (DE)

( * ) Notice: Subject to any disclaimer, the term of this patent is extended or adjusted under 35 U.S.C. 154(b) by 0 days.

(21) Appl. No.: 13/321,935

(22) PCT Filed: May 28, 2010

(86) PCT No.: PCT/EP2010/057458
§ 371 (c)(1),
(2), (4) Date: Nov. 22, 2011

(87) PCT Pub. No.: WO2010/136581
PCT Pub. Date: Dec. 2, 2010

(65) Prior Publication Data
US 2012/0084015 A1    Apr. 5, 2012

(30) Foreign Application Priority Data

May 28, 2009 (GB) .................................. 0909128.1

(51) Int. Cl.
| | | |
|---|---|---|
| *G01N 33/48* | (2006.01) | |
| *G01Q 60/42* | (2010.01) | |
| *B82Y 35/00* | (2011.01) | |
| *B82Y 15/00* | (2011.01) | |
| *G01N 33/50* | (2006.01) | |
| *G01Q 30/04* | (2010.01) | |

(52) U.S. Cl.
CPC ............ *G01N 33/5026* (2013.01); *G01Q 60/42* (2013.01); *B82Y 35/00* (2013.01); *B82Y 15/00* (2013.01); *G01Q 30/04* (2013.01)
USPC .......................................................... 702/19

(58) Field of Classification Search
None
See application file for complete search history.

(56) References Cited

U.S. PATENT DOCUMENTS 6,357,285 B1    3/2002    Allen
2001/0036293 A1*    11/2001    Laumeyer et al. ............ 382/104

OTHER PUBLICATIONS

Dickson et al. "Visualisation of mycorrhizal fungal structures and quantification of their surface area and volume using laser scanning confocal microscopy" (Mycorrhiza vol. 9 (1999) pp. 205-213).*
Bozec et al. "Atomic force microscopy of collagen structure in bone and dentine revealed by osteoclastic resorption" (Ultramicroscopy, vol. 105 (2005) pp. 79-89).*
Article—Hillebrand et al., "17β-estradiol increases volume, apical surface and elasticity of human endothelium mediated by $Na^+/H^{3O}$ exchange," *Cardiovascular Research*, vol. 69, 2006, pp. 916-924.
Article—Hillebrand et al., "How steroid hormones act on the endothelium—insights by atomic force microscopy," *Pflugers Arch—Eur J Physiol*, vol. 456, 2008, pp. 51-60.
Article—Riethmüller et al., "Vacuolar structures can be identified by AFM elasticity mapping," *Ultramicroscopy*, vol. 107, 2007, pp. 895-901.
International Preliminary Report on Patentability for PCT/EP2010/057458 dated Nov. 29, 2011, 9 pages.

* cited by examiner

*Primary Examiner* — Anna Skibinsky
(74) *Attorney, Agent, or Firm* — Dority & Manning, P.A.

(57) ABSTRACT

The present invention relates to a method based on atomic force microscopy and the use thereof on biological surfaces. A method is provided to detect the Local Deviational Volume (LDV) of defined subcellular structures irrespective of a biochemical characterization.

16 Claims, 2 Drawing Sheets

IMAGING METHOD AND USE THEREOF

FIELD OF THE INVENTION

Figure 1:
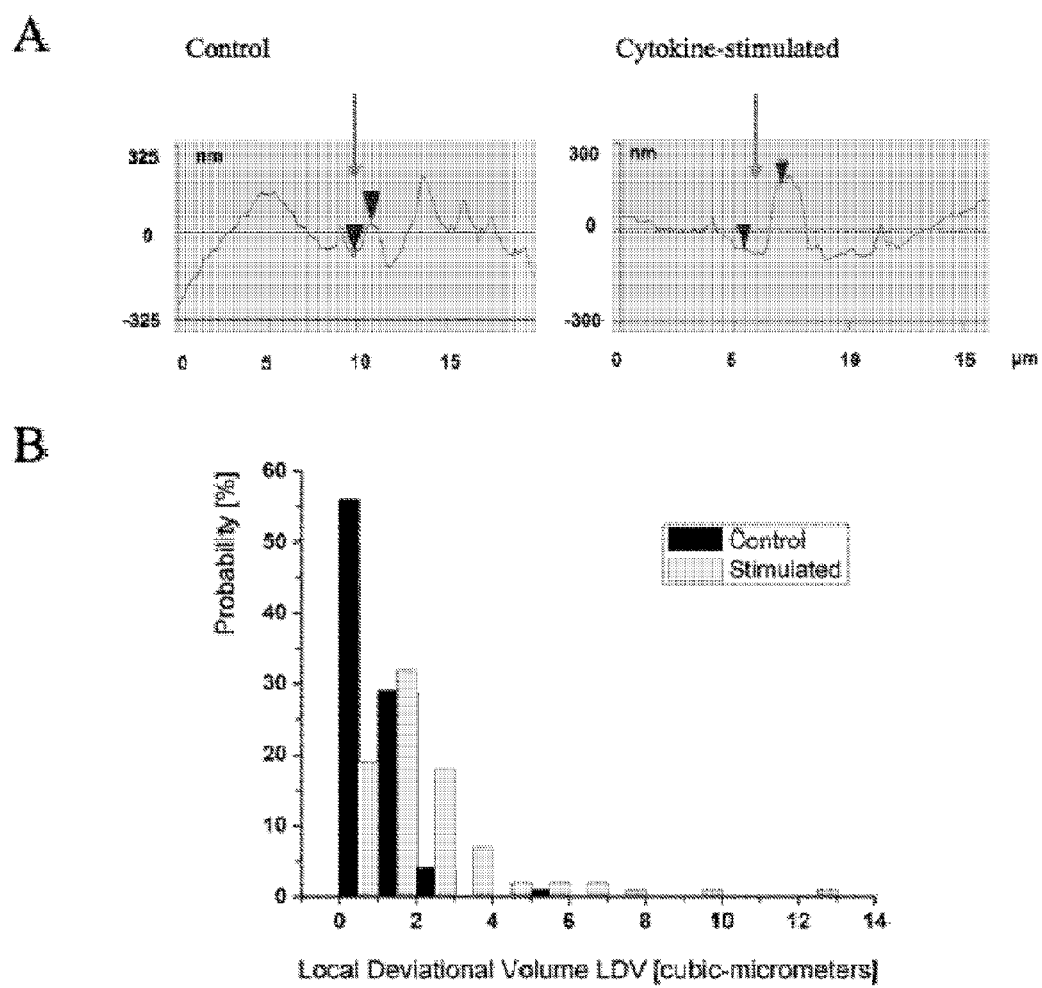

The present invention relates to a method based on atomic force microscopy and the use thereof on biological surfaces.

BACKGROUND OF THE INVENTION

Several imaging methods are known for diagnostic purposes, including the use of radioisotopes or x-ray imaging. Besides these methods, diagnostic imaging is performed on biopsies of tissues or liquids from the living body to determine the existence or cause of a disease. In the last decade imaging systems were developed using cell cultures of cells taken from a patient, in order to detect markers that are correlated to diseases. These systems are mostly based on the coupling of biological samples to defined epitopes wherein the biological samples are labelled with a dye, preferably a fluorescent dye.

Pharmacological testing and low throughput screening assays are also increasingly based on mammalian cell culture (High content screening, HCS). As compared to biochemical affinity tests used in molecular high-throughput screening (HTS), these HCS-bioassays offer the smallest living unit for detecting adverse effects on a least damage level. Thus, they can help to avoid stressing animals with pharmaceutical lead compounds. Usually, also in cell based assays, the readout is a biochemical one like DNA-, RNA- and protein-chips or immunocytochemistry or sometimes electrophysiological experiments.

Atomic force microscopy (AFM) was invented two decades ago and became a versatile tool for biological studies on single biomolecules, aggregates, viruses, cells or tissues. The method bridges the gap between the nm-resolution technique electron microscopy (EM) and the μm-scale optical microscopy (OM). As such, it combines the advantages of high resolution and the ability to investigate cells under physiological buffer conditions. At the same time, no disadvantageous sample drying or coating as necessary for EM or chromophore labelling as in fluorescence microscopy (FM) are needed. Additionally, local mechanical properties of the sample can be obtained (Riethmuller C., Schaffer T. E., Kienberger F., Stracke W. and Oberleithner H.; 2007; Ultramicroscopy 107:895-901; Rotsch C. and Radmacher M.; 2000; Biophys. J. 78:520-535). Hence, investigation of biological specimen very close to physiological conditions is possible with only a minimum of procedure-derived artifacts.

Recording the topography of biological specimen including cellular surfaces—either living or fixed—has been the basis of biologically inspired AFM studies ever since (Braet F., de Zanger R. and Wisse E.; 1997; J. Microsc. 186 (Pt 1):84-87.; Oberleithner H., Giebisch G. and Geibel, J.; 1993; Pflugers Arch. 425:506-510; Chang L., et al.; 1993; Biophys J. 64: 1282-1286). But distinct structures are difficult to identify, especially on whole cells, where only cytoskeletal structures are obviously recognisable. They almost exclusively consist of fibrillary actin, contributions of microtubuli can be neglected. However, since morphological features are difficult to classify, a reproducible quantification is hard to perform. Therefore, most studies use a qualitative, rather descriptive approach., so that often an overlay of AFM and fluorescence marker is desired to prove the claimed structure.

However, the fluorescence identification is hampered by mutually disturbing fixation protocols for AFM and FM. Unequivocally accepted structural characteristics are actin stress fibers (Haga H., Sasaki S., Kawabata K., Ito E., Ushiki T. and Sambongi T.; 2000; Ultramicroscopy 82:253-258), microvilli (Poole K., Meder D., Simons K. and Muller D.; 2004; FEBS Lett. 565:53-58) and cell junctions (Riethmuller C., Oberleithner H., Wilhelmi M., Franz J., Schlatter E., Klokkers J. and Edemir B.; 2008; Biophys. J. 94:671-678). Recently, also intracellular organelles could be identified through their specific mechanics (Riethmuller C., Schaffer T. E., Kienberger F., Stracke W. and Oberleithner H.; 2007; Ultramicroscopy 107:895-901). Beyond that, only very delicate setups can deliver more detailed information; in special cell models, where one type of receptor is abundantly expressed, some aggregates can be imaged marker-free (Hoogenboom, B. W., Suda K., Engel A. and Fotiadis D.; 2007; J. Mol. Biol. 370:246-255) or with the TREC procedure, where topography can be recorded simultaneously with localization of one specific target using antibody-modified tips (Kienberger F., Ebner A., Gruber H. J. and Hinterdorfer P.; 2006; Acc. Chem. Res. 39:29-36).

SUMMARY OF THE INVENTION

Coming from this state of the art, it is an object of the present invention to provide a method for determining and quantifying the topographical elements of biological surfaces.

The invention provides a method for determining and quantifying the topographical elements of biological surfaces using data received by atomic force microscopy, comprising the steps of a. Preparing in vitro a single cell, cellular monolayer or tissue section;

b. Determining the local deviational volume (LDV) of subcelluar structures in a predefined mask in xy-plane;

c. Normalizing the positive or negative volume of the predefined area;

d. Quantifying the local deviational volume;

e. Analysing the data by comparing them with characteristic topographical elements of a calibrated sample;

f. Evaluating the quantified structural elements to obtain parameter sets.

It is intended that the analysed area is less than the surface of one cell, wherein the cell is preferably an analysed eukaryotic, more preferably a mammalian cell. Using overlapping areas for the analysis makes it possible to obtain the overview over a larger area by assembling them.

The parameters sets that are produced with the method of the invention may be used to produce an image. It is further intended that the image showing deviational volumes can be combined with images using fluorescence for example, or other optically visible marker.

For the evaluation of the data obtained during determination of the LDV a neural network may be used, wherein the neural network comprises preferably at least three layers. For the skilled person in the art it is obvious that any other known algorithm is applicable for the evaluation of the data, even in the step of analysing the data.

The determination of the LDV takes place in a predefined part of the cellular surface, wherein the subdivided part of the cell or cell surface comprises a length of preferably 2 to 20 μm. With respect to the determination of the LDV it is intended that the subdivided part of the cell comprises a deviational volume in the range of 0.2 to 20 μm in xy-axis and <500 nm in z-axis.

The predefined mask in xy-plane for the determination of the LDV may be selected by using optical methods, comprising phase contrast, fluorescence or raman microscopy. Thus, the area for applying the disclosed method is chosen in a further embodiment by optical microscopy before the determination and quantification of topographical elements of the biological surfaces takes place.

It is intended that the calibrated sample comprises data of cell surface marker, topographical or morphological structures. The data of the calibrated or standard sample are obtained preferably by the optical identification of cell surface marker or morphological structures. Specific patterns are used for the generation of a classification set or a classification matrix that is related to one or more diseases. It is also possible that the data of the calibrated sample are obtained by analysing the interaction of biochemical marker with topographical or morphological structures.

According to the invention the cell surface marker comprise topographical or morphological structures like protrusions, depressions or other morphological structures or combinations thereof or specific patterns of such structures.

It is intended that the method according to the invention is used to produce a map of topographical elements or for in vivo and in vitro mapping and quantifying of cell surface marker, topographical or morphological structures on cell surfaces or surfaces of cell junctions.

The method according to the invention is intended for the detection of specific cell surface marker, topographical or morphological structures related to diseases, wherein the diseases are chosen from the group of tumour, cardiovascular, nephritic, fibrotic, inflammatory, arteriosclerotic or auto-immune diseases. It is obvious for a person skilled in the art that the present invention is not limited to the listed diseases but also applicable to any disease that is accompanied with topographical or morphological changes of the cell surface.

The method according to the invention is further intended for determining cell surface marker, topographical or morphological structures as diagnostic marker or monitoring changes of cell surface marker, topographical or morphological structures in the prophylaxis, diagnosis, therapy, follow-up and/or aftercare of a therapy in any of the diseases mentioned above. Besides this the method is suitable and intended for determining cellular mechanical or contractile forces.

The method according to the invention may be used in the production or screening of a drug for the treatment of any of the diseases mentioned above comprising pharmaceutical compositions, antibodies, proteins, peptides, nucleic acids or chemicals, but is not limited to this substances.

The method according to the invention is also intended for a cell-culture based classification system in diagnosis. Specific patterns of topographical or morphological structures will be related to disease induced changes of the cell surface, so that changes of the cell surface can be used for the identification of specific disease patterns. Additionally it is possible to determine the local extension of a disease, if cell samples from different parts of the body are used as template for the method according to the invention The present invention provides a method to determine the Local Deviational Volume (LDV) of defined subcellular structures irrespective of their biochemical characterisation while disregarding the lack of knowledge about their exact cellular function. The LDV shall define a nanoscale excursion in z-direction (height) over an expected mask in the xy-plane, no matter whether they are circular or not and whether they are positive or negative in z. They use a fuzzy definition of patterning elements. Then, the local protruding or depressed volume as compared to the mean surface level is evaluated. The new method bases on the observation that the surface texture changes within a nanometer range in z (height), when cells are growing, developing, differentiating or are being stressed or undergo a transformation. Moreover, their physiological function sometimes correlates to the LDV in some respect.

The type of stimulus leads to distinct alterations in target cell models. Some examples are:
a. Collecting duct epithelial cells not only show protruding borders, but also central cilia, that indicate the degree of differentiation within the cell preparation.
b. Virtually all endothelial cells form stress fibers, when challenged, resulting in a markedly structured cytoskeleton, the quantitation of which would give a stress factor.
c. Kidney tubule cells react to an increased intracellular tension via reinforcement of their junctions (unpublished). The LDV at the cell border can be taken as a measure for a cell layer's reactance against stress.
d. Endothelial cells are key to the control of leukocyte invasion into an inflamed tissue. The process of transmigration is not completely understood, but the endothelial role has been underestimated. Recently, we found, that the endothelial cell softens underneath the leukocyte to let it pass through (unpublished). To initiate this step, the endothelium prepares by altering its LDV at putative sites of transmigration. Quantification of this LDV can be used to give a (pro-)inflammatory index.

When quantitated, the above listed alterations can be used for determination of a cell's status in various kinds of cellular disease models up to the development of diagnostic assays. One advantage of this method is its applicability to cells on biomaterials, which are not suited for optical microscopy like metals, minerals or microporous membranes. Successful linking of Bio-AFM to diagnostic procedures has not been reported so far.

It is possible to apply the method of the invention on known xy-axis data in order to record data for the z-axis or to obtain the local deviation volume.

The data of the standard sample are obtained preferably by the optical identification of cell surface marker or morphological structures. Specific patterns are used for the generation of a classification set or a classification matrix that is related to one or more diseases.

We here open up a possibility to classify and quantify the three-dimensionsional nanoarchitecture of cells as a holistic approach to evaluating a cell's biological status.

DETAILED DESCRIPTION OF THE INVENTION

The invention will be further described by figures and examples without being limited to the described embodiments:

The invention is based on the experimental results, that the surface texture changes on the nanoscale, when cells are developing, are being stressed or undergo a transformation. Using the method according to the invention it was for the first time possible to show that the type of stimulus leads to distinct alterations in target cell models.

Samples and AFM was performed as follows:
Sample Preparation

Living cells were subjected to AFM-imaging either directly in growth medium or in physiological HEPES buffer (in contact mode using gold coated standard AFM tips) without further preparation.

Fixed Samples

After time intervals determined by the experimental model and specific question, the cell samples were fixed with glutardialdehyde (0.05% to 5% final concentration for 1-100 min in growth medium under physiological conditions (37° C., 19% $O_2$, 5% $CO_2$) or in buffer at room temperature. If applicable, filter membranes were cut out and subjected to AFM contact imaging in HEPES buffered solution at room temperature (20° C.). Images were taken with a Bioscope (Nanoscope IIIa Controller, Digital Instruments, Calif., Santa Barbara, USA) using gold-coated MLCT-AUNM tips (spring constant 0.01 N/m) in contact mode.

AFM

To obtain maximal resolution in z-height, the AFM was mounted on a specially designed construction for minimising the ambient mechanical noise. To isolate the setup well from vibration, it was put on an air cushioned table, which in turn bears a platform being suspended on rubber strings. Moreover, the whole construction was shielded by a foam-coated acoustic hood. Additionally, careful grounding of metal parts was performed to reduce electrical noise. Parameters in the software were always optimised for lowest noise and least artefact generation. The noise of the instrumentation using conditions as stated below was measured on atomically flat mica to yield <0.5 nm of mean roughness. The force exerted on the sample was kept below 5 nN, the scan rates were 0.5-10 Hz/line and digital resolution usually was from $128^2$ to $1024^2$ pixels.

Images were processed using the Nanoscope software, version 5.12b48 which is supplied by the manufacturer (Digital Instruments). Image analysis and presentation was performed with the software SPIP (Scanning probe image processor V 3.3.9, Image Metrology, Lyngby, Denmark).

Force-volume imaging: To obtain the Young's Modulus (YM) quantifying the stiffness of the samples, 64*64 arrays of force-distance curves were recorded in "force volume" mode which records the deflection of the cantilever (in nm) as a function of piezo elongation (z-distance in nm). Piezo z travel speed was kept below 10 µm/s. In order to reconstruct the respective maps for height and Young's Modulus (YM), raw data were processed with a routine written for the software "Igor Pro" based on the Hertz' model of elasticity as described in previous studies by M. Radmacher et al. (Science; 1992; 257: 1900).

The following examples were performed by using the method according to the invention:

1. Determination of a "Stress Factor"

Virtually all cells react to stress when challenged, resulting in a markedly structured cytoskeleton, the quantitation of which would give a "stress factor".

Cell Isolation and Cultivation:

Cells are cultivated along standard biological protocols applicable for growth of the specific cells. Livings cells are extremely soft—especially at 37° C. when the cellular surface basically is a fluid, as well as the cytosol. Hence, upon minute mechanical loads, they readily deform until a harder structure becomes detectable, which represent polymeric actin bundles. These fibers are quickly reorganised by cells upon physiological or noxious stimuli. The mediators of this profibrotic signaling may be among cytokines, interleukins, growth factors, (peptide) hormones etc. Due to the altered mechanical characteristics, physiological function of the cells may be inhibited, eventually leading to a pathophysiological cellular state.

Results

Through morphometrical analysis by the method according to the invention, the amount of fiber-formation can be quantified. Moreover, stiffness measurements (mechanical quantification via determination of Young's Modulus) can give the sum of local effects.

Cellular fibers have been investigated so far by fluorescence microscopy, which usually requires fixed samples and does not yield quantitative results. The latter method has the disadvantage of a high fluorescence background due to monomeric GFP-actin. Additionally, it requires optically transparent media, preferably glass to grow the cells on.

2. Determination of cell Differentiation

Collecting duct epithelial cells exhibit protruding borders, when being highly differentiated. Moreover, also central cilia develop, that can indicate the degree of differentiation within the cell preparation.

Cell Isolation and Cultivation:

Inner medulla collecting duct (IMCD) epithelial cells were prepared as follows:

Briefly, the inner medullas of deceased Wistar rats were removed, cutted into small pieces and digested in PBS (Biochrom, Berlin, Germany) containing 0.2% hyaluronidase (Sigma, Germany) and 0.2% collagenase type CLS-II (Sigma, Germany) at 37° C. for 90 min. The cells were seeded on glass cover slips coated with collagen type IV (Becton-Dickinson, Heidelberg, Germany) at a density of approximately $10^5$ cells/cm$^2$ and cultivated in Dulbecco's modified Eagle's medium (DMEM) containing penicillin 100 IU/ml and streptomycin 100 µg/ml, 0.2% glutamine, 1% non essential amino acids. The osmolarity was adjusted to 600 mosmol/l by the addition of 100 mM NaCl and 100 mM urea. To maintain AQP2 expression 10 µM di-butyryl-cAMP was added. The cells were cultured for 5-7 days and the dbcAMP was removed 14-18 h prior to the experiments.

Results

AFM-images obtained with the method according to the invention of IMCD cells demonstrated for the first time, that cell border structures do not necessarily invaginate, but can protrude up to 300 nm above the level of the cell body. The local deviational volume (LDV) correlates to the degree of tissue differentiation. The latter can be estimated from the regularity of the hexagonal lattice of cells. Another indicator is the existence of central humps, measuring around 1 µm (including tip convolution) in diameter and 0.5 up to 2 µm in height. These can only be interpreted as central cilia, flow sensors of the cells, which preferentially appear on very well developed regions. These structures can be taken to indicate the degree of differentiation, both through their height and LDV.

3. Determination of cell Tension

Kidney tubule cells respond to an elevated intracellular tension via reinforcement of their junctions. Subsequently they form a seam, the LDV of which can be taken as an indirect measure for reactance to stress.

Cell Isolation and Cultivation

The epithelial cell line NRK-52E (being cloned from a mixture of normal rat kidney cells) was received from the Deutsche Sammlung von Mikroorganismen und Zellkulturen GmbH (DSMZ, Braunschweig, Germany). Cells were propagated and cultured in Dulbecco's Minimum Essential Medium (DMEM) containing 4.5 g/l D-glucose and 3.7 g/l NaHCO$_3$ (Biochrom, Berlin, Germany) supplemented with 10% fetal calf serum (PAA, Linz, Austria), 2 mM L-glutamin (Biochrom, Berlin, Germany) as well as 100 [g/ml Penicillin and 100 [g/ml Streptomycin (Biochrom). Cells were routinely passaged once a week (1:10). All cell cultures were maintained at 37° C. in a humidified atmosphere of 5% CO$_2$-95% air. Cells were seeded into 6- and 12-well plates containing 15 mm or 24 mm coverslips which were partially gold-covered (50 nm) for AFM experiments. Cells were grown to confluence on all substrates used and the cell culture medium was exchanged 24 h prior to any experiment.

Results

Control cells appear like typical epithelial cells do; they form a cobblestone-like layer with high nuclear regions, decorated by microvilli and separated by furrow-type cell borders. After stimulation with cytokine for at least 30h, they not only develop stress fibers and elongate in shape, but they also form punctuate cell borders. These borders eventually protrude above cytosolic level up to 300 nm. This effect is accompanied by an increase in overall cell stiffness of 70%. The protrusions obviously are a counter-regulatory response of the cells to elevated intracellular tension. A quantification of the LDV gives a measure for the degree of transdifferentiation from an epithelial to a mesenchymal state. This measure has been proven sensitive to force-inhibiting agents and hence can report on the tensional status of a cell culture and its physiological barrier function.

4. Determination of Inflammatory Status

Endothelial cells are key to the control of leukocytes invading an inflamed tissue. The process of transmigration (diapedesis) is not completely understood, but the endothelial role has been underestimated. The inventors were able to demonstrate that the endothelial cytoskeleton softens underneath the leukocyte to let it pass through (unpublished data). To initiate this step, the endothelium prepares itself by altering its LDV at putative sites of transmigration. Quantification of LDV in these regions would give an estimate of a pro-inflammatory index.

Cell Isolation and Cultivation

Human umbilical cords were obtained from normal births. Endothelial cells (HUVEC) were prepared as described. Briefly, veins were treated with collagenase and grown on gelatine coated culture flasks in a humidified chamber at 37° C., 5% $CO_2$ in M199 Medium (Gibco, purchased through Invitrogen, Karlsruhe, Germany) containing penicilline/streptomycine, heparin and 10% freshly isolated human serum. 10 h prior to imaging, they were stimulated with proinflammatory cytokines, which can also recruit from the group of interleukins, hormones, growth factors asf.

Results

After having developed a special kind of AFM-manipulation method ("nano-surgery") to specifically remove firmly adhering leukocytes (§Riethmüller 2008), the inventors found the border of the interaction-site decorated with filopodia-like protrusions. These protrusions grasp for the leukocyte to engulf it. They are mechanically softer than the cytosol and measure 150 nm in height and up to 2 µm in length. These finger-like protrusions are propelled from endothelial surface, thereby proving the essential role of endothelial cells in diapedesis. Therefore, quantitation of these morphological structures could give at hand a readout parameter for the transmigratory capacity (permissivity) of an endothelial cell culture. This could help to estimate the pro- or anti-inflammatory potential of pharmaceutical compounds in cell based assays.

The figures show

FIG. 1 A) Height profiles on epithelial cell surface under fluid buffer conditions as described in example 3). A representative profile of control (left) and stimulated (right) sample is shown. A typical protrusion of 150 nm in height and 1.5 µm diameter is marked by triangles (right).

B) Size distribution of the local deviational volume (LDV) derived from specific surface structures. Histograms showing LDV of membrane protrusions are given in control or cytokine-stimulated of epithelial cells from kidney in culture. The most probable LDV value shifts from 0.6 to 1.9 $\mu m^3$ upon three days of cytokine treatment.

Figure 2:
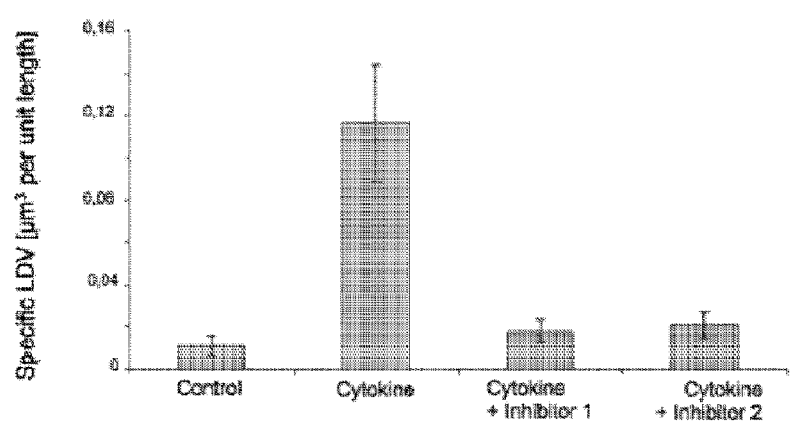

FIG. 2 Pharmacological intervention as quantified via Specific LDV. In a cellular model of inflammation, the LDV values are quantitated and divided by cell border length to yield the Specific LDV independent of cell size. Inhibition of the cytokine-induced signalling reduced the Specific LDV almost down to control values

The invention claimed is:

1. A method for determining and quantifying the topographical elements of biological surfaces using data received by atomic force microscopy, comprising the steps of:
   a. Preparing in vitro a single cell, cellular monolayer, or tissue section;
   b. Predefining, using a processor, a mask in an xy-plane on a subdivided part of a cellular surface comprising subcellular structures of the single cell, cellular monolayer, or tissue section;
   c. Determining, using a processor, the local deviational volume (LDV) of the subdivided part in the predefined mask in the xy-plane by: (i) determining nanoscale excursions in a z-direction over the predefined mask in the xy-plane of a subcellular surface; ii evaluatng a local protruding (positive) and depressed (negative) volume as compared to a mean surface level of the predefined mask: and (iii) normalizing the positive and negative volume within the predefined mask; and
   d. Assembling, using a processor, predefined masks, wherein each mask has a determined LDV, for subdivided tarts of a cellular surface, into a combined lager area. wherein the masks overlap, and determining an image showing deviational volumes.

2. The method of claim 1, wherein the predefined mask is less than the surface area of one cell.

3. The method of claim 2, wherein the cell is a eukaryotic cell.

4. The method of claim 3, wherein the cell is a mammalian cell.

5. The method of claim 1, wherein the local deviational volume of the subdivided parts is analyzed by a neural network, wherein the neural network comprises at least three layers.

6. The method of claim 1, wherein the predefined mask comprises a length of 2 micrometers to 20 micrometers.

7. The method of claim 1, wherein the predefined mask comprises a deviational volume in the range of 0.2 micrometers to 20 micrometers in the xy-axis and less than 500 nanometers in the z-axis.

8. The method of claim 1, wherein the calibrated sample comprises data of cell surface markers, topographical structures, or morphological structures.

9. The method of claim 8, wherein the cell surface markers, topographical structures, or morphological structures comprise protrusions, depressions, specific patterns of protrusions or depressions, or combinations thereof.

10. The method of claim 1, wherein the method maps and quantifies cell surface markers, topographical structures, and morphological structures on cell surfaces or surfaces of cell junctions in vitro or in vivo.

11. The method of claim 10, wherein the cell surface markers, topographical structures, or morphological structures are related to diseases chosen from the group of tumour, cardiovascular, nephritic, fibrotic, inflammatory, arteriosclerotic, or auto-immune diseases.

12. The method of claim 1, wherein the parameter sets are used to produce a map of multiple topographical elements for quantifying cell surface markers, topographical structures, and morphological structures.

13. The method of claim 1, wherein the method further comprises monitoring for changes local deviational volume in cell surface markers, topographical structures, or morphological structures in the prophylaxis, diagnosis, therapy, follow-up, or aftercare of a therapy in tumour, cardiovascular, nephritic, fibrotic, inflammatory, arteriosclerotic, or auto-immune diseases.

14. The method of claim 1, wherein the method further comprises determining cellular mechanical or contractile forces.

15. The method of claim 1, wherein the predefined mask in the xy-plane is determined by optical methods comprising phase contrast, fluorescence, or raman microscopy.

16. The method of claim 1, wherein changes in the topographical elements of the subcellular structures are due to the growth, development, differentiation, or transformation of cells.

\* \* \* \* \*